(12) United States Patent
Chu

(10) Patent No.: US 7,648,705 B2
(45) Date of Patent: Jan. 19, 2010

(54) METHODS FOR PREVENTION OR AMELIORATION OF WEST NILE ENCEPHALITIS USING A WEST NILE DNA VACCINE

(75) Inventor: Hsien-Jue Chu, Overland Park, KS (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 11/589,507

(22) Filed: Oct. 30, 2006

(65) Prior Publication Data
US 2007/0166802 A1 Jul. 19, 2007

Related U.S. Application Data

(62) Division of application No. 10/202,716, filed on Jul. 25, 2002, now Pat. No. 7,153,513.

(60) Provisional application No. 60/308,334, filed on Jul. 27, 2001.

(51) Int. Cl.
A61K 39/00 (2006.01)
A61K 45/00 (2006.01)
A61K 31/711 (2006.01)

(52) U.S. Cl. .................... 424/218.1; 424/283.1; 514/44

(58) Field of Classification Search ............. 424/204.1, 424/218.1, 155.1, 190.1, 202.1, 199.1; 435/69.1, 435/173.3
See application file for complete search history.

(56) References Cited

U.S. PATENT DOCUMENTS

| 6,184,024 B1 | 2/2001 | Lai et al. |
| 6,235,282 B1 | 5/2001 | Riviere et al. |
| 7,227,011 B2 * | 6/2007 | Chang .................... 536/23.72 |
| 2002/0164349 A1 | 11/2002 | Weiner et al. |
| 2003/0022849 A1 * | 1/2003 | Chang .................... 514/44 |
| 2003/0104008 A1 | 6/2003 | Loosmore et al. |

FOREIGN PATENT DOCUMENTS

| WO | WO 94/20071 A | 9/1994 |
| WO | WO 95/30437 A | 11/1995 |
| WO | WO 99/63095 | 12/1999 |
| WO | WO 02/068637 A2 | 9/2002 |
| WO | WO 02/072036 A2 | 9/2002 |
| WO | WO 02/081621 A2 | 10/2002 |
| WO | WO 02/081754 A1 | 10/2002 |
| WO | WO 02/083903 A2 | 10/2002 |
| WO | WO 2004/016586 A2 | 2/2004 |

OTHER PUBLICATIONS

Davis et al (Journal of Virology 75:4040-4047, May 2001) (cited in IDS).*
Chang et al. Journal of Virology, May 2000, p. 4244-4252 vol. 74, No. 9 (cited in IDS).*
S. Lustig et al.; Viral Immunology, Mary Ann Liebert, Inc., New York,. US; vol. 13, No, 4; pp. 401-410; 2000.
T. P. Monath et al.; Current Drug Targets, Bentham Science Publisher, US: vol. 1. No. 1; pp. 37-50; 2001.
A. C. Allison; Methods: A Companion to Methods in Enzymology, Academic Press Inc., New York, NY, US; vol. 19; pp. 87-93; 1999.
J. Arroyo et al.: Trends in Molecular Medicine, Elsevier Current Trends; vol. 7, No. 8; pp. 350-354; 2001.
Steele et al., "Pathology of Fatal West Nile Virus Infections in Native and Exotic Birds During the 1999 Outbreak in New York City, NY." Veterinary Pathology (2000) vol. 37, pp. 208-224.
Hammon, W. McD et al., "Immunity of Hamsters to West Nile and Murray Valley Viruses Following Immunization with St. Louis and Japanese B.", Proc. Soc. Exper. Biol. & Med, (1956), vol. 91, pp. 521-523.
Xiao, S. et al., "West Nile Virus Infection in the Golden Hamster (*Mesocricetus auratus*): A Model for West Nile Encephalitis", Centers for Disease Control, Jul.-Aug. 2001, vol. 7, No. 4, Entire 14-page Article.
Price et al., "Live and Inactivated Vaccines of Group B Arboviruses: Role of Neutralizing Antibody and Serum Protective Factor", Nature (1969) vol. 222, pp. 1294-1295.
Imam et al., "Challenge of Hamsters with Japanese B. St. Louis and Murray Valley Encephalitis after Immunization by West Nile Infection Plus Specific Vaccine", Journal of Immunology (1957) vol. 79, No. 3, pp. 243-252.
Anderson, J et al., "Isolation of West Nile Virus from Mosquitoes, Crows, and a Cooper's Hawk in Connecticut", Science, Dec. 17, 1999, vol. 286, pp. 2331-2333.
Senne, D. et al., "Pathogenicity of West Nile Virus in Chickens", Avian Diseases, (2000), vol. 44, pp. 642-649.
Davis, B. S. et al., "West Nile Virus Recombinant DNA VAccine Protects Mouse and Horse from Virus Challenge and Expresses In Vitro a Noninfectious Recombinant Antigen That can be Used in Enzyme-Linked Immunosorbent Assays", Journal of Virology, May 2001, vol. 75, No. 9, pp. 4040-4047.
Chang, G. J. et al, "A single Intramuscular Injection of Recombinant Plasmid DNA Induces Protective Immunity and Prevents Japanese Encephalitis in Mice", Journal of Virology, May 2000, vol. 74, No. 9, pp. 4244-4252.

* cited by examiner

Primary Examiner—Mary E Mosher
(74) Attorney, Agent, or Firm—Maria Restrepo-Hartwig

(57) ABSTRACT

The present invention provides a safe and effective vaccine composition against West Nile virus disease. An immunogenically active component of West Nile virus or plasmid DNA, an adjuvant such as a metabolizable oil, and a pharmacologically acceptable carrier are formulated into an immunizing vaccine. The invention also provides a method for the prevention or amelioration of West Nile disease, such as encephalitis, in equidae by administering the vaccine composition herein set forth.

10 Claims, No Drawings

METHODS FOR PREVENTION OR AMELIORATION OF WEST NILE ENCEPHALITIS USING A WEST NILE DNA VACCINE

CROSS-REFERENCE TO RELATED APPLICATIONS

This application is a divisional of U.S. application Ser. No. 10/202,716, filed on Jul. 25, 2002, now U.S. Pat. No. 7,153,513, which claims priority from U.S. application Ser. No. 60/308,334 filed on Jul. 27, 2001.

FIELD OF THE INVENTION

The present invention relates to safe and effective West Nile Virus vaccines, and to methods of administering same to mammals, in particular horses.

BACKGROUND OF THE INVENTION

Known as a Flavivirus, the West Nile virus was first identified in 1937 in Africa and first found in North America in 1999. Migratory birds are considered the primary means whereby infection is spread within and between countries. The virus is transmitted by mosquitoes that have acquired infection by feeding on viremic birds. The virus is then amplified during periods of adult mosquito blood-feeding. Infected mosquitos then transmit the virus to humans and animals upon feeding thereon.

West Nile virus is the causative agent for West Nile Virus disease, particularly West Nile encephalitis, predominately in humans, other mammals and birds. The chief concern in both the United States and foreign countries is the lack of effective treatment for West Nile virus disease. Anti-inflammatory drugs are used to combat swelling of central nervous system tissues, but beyond that no medical intervention is available. Nor is there believed to be a suitable vaccine known to prevent the infection. To date, preventing contact with carriers appears to be the only means of controlling the West Nile virus.

What is therefore needed in the art is to provide a safe and effective equine West Nile virus vaccine composition. The vaccine composition should be sufficiently safened so as to be suitable for administration even to pregnant mares without adverse effect.

Also needed is a method for the prevention or amelioration of West Nile Virus disease, particularly West Nile encephalitis, in equidae and other mammals.

SUMMARY OF THE INVENTION

The present invention provides a safened vaccine composition which comprises: an effective immunizing amount of an immunogenically active component selected from the group consisting of an inactivated whole or subunit West Nile virus, an antigen derived from said virus, DNA derived from said virus, and a mixture thereof; an immunogenically stimulating amount of a metabolizable oil; and a pharmacologically acceptable carrier.

The present invention also provides a method for the prevention or amelioration of West Nile encephalitis in equidae which comprises administering to said equidae a safened vaccine composition which comprises an effective immunizing amount of an immunogenically active component selected from the group consisting of an inactivated whole or subunit West Nile virus, an antigen derived from said virus, DNA derived from said virus, and a mixture thereof; an immunogenically stimulating amount of a metabolizable oil; and a pharmacologically acceptable carrier.

Also provided as part of the invention is a safe and effective West Nile Virus vaccine suitable for use in horses which comprises an immunogenically active component selected from the group consisting of an inactivated whole or subunit West Nile virus, an antigen derived from said virus, DNA derived from said virus, and a mixture thereof; an immunogenically stimulating amount of a metabolizable oil; and a pharmacologically acceptable carrier.

In a further embodiment, the invention describes a vaccine composition comprising at least about at least about $1 \times 10^4$ $TCID_{50}$ per unit dose of inactivated West Nile virus, or a component thereof, and about 4% to 10% vol/vol of a metabolizable oil comprising about 1 to 3% polyoxyethylene-polyoxypropylene block copolymer, about 2 to 6% of squalane and about 0.1 to 0.5% of polyoxyethylene sorbitan monooleate.

Further provided is a safened and effective West Nile virus vaccine for equidae, comprising at least about $1 \times 10^6$ $TCID_{50}$ per unit dose of killed or inactivated West Nile virus, and at least about 1% vol/vol of an adjuvant comprising at least one metabolizable oil and at least one wetting or dispersing agent.

The invention also sets forth a vaccine regimen for horses, comprising two dosage units of killed or inactivated West Nile virus, wherein each said dosage unit comprises about 0.5 to 5 milliliters of a composition containing at least about $5 \times 10^7$ $TCID_{50}$ of said virus and about 1 to 10% vol/vol of an adjuvant, said adjuvant comprising at least one metabolizable oil and at least two nonionic surfactants, and further wherein said dosage unit comprises a pharmacologically acceptable carrier.

Also provided as part of the invention is an equine vaccine containing West Nile plasmid DNA in an amount of about 50 to 3,000 micrograms per dose, together with one or more adjuvants and a suitable carrier. A vaccine regimen would comprise administering at least about one dose of this composition, and desirably at least about 2 doses, to horses for immunization against West Nile virus disease.

Further, objects and features of the invention will become apparent from the detailed description and the claims set forth herein below.

DETAILED DESCRIPTION OF THE INVENTION

Scientists believe that the West Nile virus follows the same pattern of infection found with other mosquito-transmitted viruses. When an infected mosquito bites an equid, the virus enters the skin or tissues just below the bite site, where it is picked up by the circulation. The virus can multiply in the bloodstream, and the equid may develop a fever, which often goes undetected because there are no other signs of illness at the time. However, once the virus has invaded the nervous system, clinical signs appear within one to three days. Most affected equidae, such as horses, first exhibit signs of posterior weakness or paralysis and poor coordination. Depression and related behavior changes may accompany the physical changes. In severe cases, tremors, convulsions, paddling of the limbs and paralysis may develop. Severe neurological problems and mortality have also been observed. To date, no vaccine known to prevent West Nile virus in equidae is available; and the only means of controlling the West Nile virus appears to be the prevention of contact with a carrier.

It has now been found that a safe and effective vaccine composition which comprises an effective immunizing amount of an immunogenically active component selected from the group consisting of an inactivated whole or subunit West Nile virus, an antigen derived from said virus, DNA derived from said virus, plasmid West Nile virus DNA, plasmid with sequence inserts of said virus, and a mixture thereof; an immunogenically stimulating amount of an adjuvant, in particular a metabolizable oil; and a pharmacologically acceptable carrier may be administered to equidae, particularly horses, to prevent or ameliorate West Nile Virus disease such as encephalitis.

DNA derived from the West Nile virus may be obtained via isolation from sources such as the fluids or tissues of equine or avian species diagnosed to have West Nile encephalitis. Such sources include cerebral spinal fluid or sections of spinal cord or brain. DNA may also be obtained using other available techniques such as plasmid technology. For example, suitable cells of an organism, e.g. *E. coli*, may be transformed with a plasmid containing West Nile protein sequence inserts to obtain a master seed. The master seed may then be cultured and passaged. Transformed cells containing the West Nile DNA may then be harvested, and the DNA isolated and obtained using techniques available to the skilled artisan.

Whole or subunit West Nile virus may be isolated from infected animals using conventional techniques. Samples of the virus may also be obtained from tissue culture collections which maintain a depository for organisms such as West Nile. At the American Type Culture Collection (ATCC), for example, the West Nile virus has been deposited under ATCC No.s VR-82, VR-1267 and VR-1267 AF.

Whole or subunit West Nile virus may be inactivated by conventional inactivating means, for example chemical inactivation using chemical inactivating agents such as binary ethyleneimine, beta-propiolactone, formalin, gluteraldehyde, sodium dodecyl sulfate, or the like or a mixture thereof, preferably formalin. Said virus may also be inactivated by heat or psoralen in the presence of ultraviolet light. (Live, attenuated West Nile virus may also be used in certain embodiments, but this is perhaps much less preferred.)

Whole or subunit West Nile virus may be maintained or grown in mouse brains or in suitable tissue culture media, such as optiMEM (LTI, Grand Island, N.Y.) or MEM media, or in cells known in the art such as African green monkey kidney (Vero) cells or baby hamster (BHK) cells, preferably Vero cells. Said virus may then be separated from the tissue culture or cell media using conventional techniques such as centrifugation, filtration or the like.

A preferred West Nile virus isolate may be obtained from the National Veterinary Services Laboratory (part of the United States Department of Agriculture) in Ames, Iowa as strain VM-2. The virus strain may be plaque purified up to three times, and passaged to X+5 in Vero cells.

As used herein the term "immunogenically active" designates the ability to stimulate an immune response, i.e., to stimulate the production of antibodies, particularly humoral antibodies, or to stimulate a cell-mediated response. For example, the ability to stimulate the production of circulating or secretory antibodies or the production of a cell-mediated response in local mucosal regions, (e.g., intestinal mucosa), peripheral blood, cerebral spinal fluid or the like.

The effective immunizing amount of the immunogenically active component may vary and may be any amount sufficient to evoke an immune response and provide immunological protection against West Nile Virus disease. Amounts wherein a dosage unit comprises at least about $1 \times 10^4$ TCID$_{50}$ of killed or inactivated whole or subunit virus cells or antigen or DNA cells derived therefrom or a mixture thereof, preferably at least about $1 \times 10^6$ TCID$_{50}$, are suitable. Even more preferably, at least about $1 \times 10^7$ TCID$_{50}$ per dosage unit may be utilized.

It is especially desirable that at least about $5 \times 10^7$ TCID$_{50}$ of killed or inactivated whole or subunit West Nile virus cells or antigen or DNA cells derived therefrom or a mixture thereof be used in the vaccine composition of the invention. In certain embodiments, as much as $1 \times 10^9$ TCID$_{50}$ and more may be utilized. A range of about $1 \times 10^4$ TCID$_{50}$ to about $1 \times 10^8$ TCID$_{50}$ may also be utilized.

In a further embodiment of the invention, it is contemplated that about 50 to 3,000 micrograms (μg or $10^{-6}$ grams) of West Nile plasmid DNA may be utilized in one dosage unit of the vaccine composition. More preferably, about 100 to 1,000 μg may be used, with about 100 to 250 μg of plasmid DNA being more preferred.

At least one dosage unit per animal is contemplated herein as a vaccination regimen. In some embodiments, two or more dosage units may be especially useful. A dosage unit may typically be about 0.1 to 10 milliliters of vaccine composition, preferably about 0.5 to 5 milliliters, and even more preferably about 1 to 2 milliliters, with each dosage unit containing the heretofore described quantity of virus or virus component. The skilled artisan will quickly recognize that a particular quantity of vaccine composition per dosage unit, as well as the total number of dosage units per vaccination regimen, may be optimized, so long as an effective immunizing amount of the virus or a component thereof is ultimately delivered to the animal.

The West Nile virus vaccine composition of the invention may also contain one or more adjuvants. As used herein the term "adjuvant" refers to any component which improves the body's response to a vaccine. The adjuvant will typically comprise about 0.1 to 50% vol/vol of the vaccine formulation of the invention, more preferably about 1 to 50% of the vaccine, and even more desirably about 1 to 20% thereof. Amounts of about 4 to 10% may be even more preferred.

Suitable adjuvants can include immunostimulating oils such as certain metabolizable oils. Metabolizable oils suitable for use in the composition of the invention include oil emulsions, e.g., SP oil (hereinafter described), Emulsigen (MPV Laboratories, Ralston, NZ), Montanide 264,266,26 (Seppic SA, Paris, France), as well as peanut oil and other vegetable-based oils, squalane (shark liver oil) or other metabolizable oil which can be shown to be suitable as an adjuvant in veterinary vaccine practice.

In addition, the adjuvant may include one or more wetting or dispersing agents in amounts of about 0.1 to 25%, more preferably about 1 to 10%, and even more preferably about 1 to 3% by volume of the adjuvant. Particularly preferred as wetting or dispersing agents are non-ionic surfactants. Useful non-ionic surfactants include polyoxyethylene/polyoxypropylene block copolymers, especially those marketed under the trademark PLURONIC® and available from BASF Corporation (Mt. Olive, N.J.). Other useful nonionic surfactants include polyoxyethylene esters such as polyoxyethylene sorbitan monooleate, available under the trademark TWEEN 80®. It may be desirable to include more than one, e.g. at least two, wetting or dispersing agents in the adjuvant as part of the vaccine composition of the invention.

Other components of the adjuvant may include such preservative compounds as formalin and thimerosal in amounts of up to about 1% vol/vol of the adjuvant.

As an adjuvant, SP oil is preferred. As used in the specification and claims, the term "SP oil" designates an oil emulsion comprising a polyoxyethylene-polyoxypropylene block copolymer, squalane, polyoxyethylene sorbitan monooleate and a buffered salt solution. In general, the SP oil emulsion will comprise about 1 to 3% vol/vol of block copolymer, about 2 to 6% vol/vol of squalane, more particularly about 3 to 6% of squalane, and about 0.1 to 0.5% vol/vol of polyoxyethylene sorbitan monooleate, with the remainder being a buffered salt solution.

When utilized, immunogenically stimulating amounts of SP oil as adjuvant in the vaccine composition of the invention may vary according to the immunogenically active component, the degree of potential infectious exposure, method of administration of the vaccine composition, the age and size of the equid, or the like. In general, amounts of about 1% to 50% vol/vol, preferably about 4% to 10% vol/vol, and more preferably about 4% to 5% vol/vol of SP oil are suitable.

In general, it is believed that a live virus vaccine may potentially lack sufficient safety in a given target host, and that a killed or inactivated virus vaccine may potentially lack the ability to stimulate a sufficiently effective immunologic response. Commonly, an adjuvant or immunogenically stimulating compound is used in combination with a killed or inactivated virus in a vaccine composition to obtain acceptable efficacy. However, safety to the target host is often compromised by the addition of an adjuvant. For example, pregnant animals many times have been known to have a significantly higher rate of miscarriage after being administered a killed or inactivated virus vaccine that contains an adjuvant.

It has now been found that when a suitable adjuvant, e.g. a metabolizable oil preferably such as SP oil, is used in combination with an immunogenically active component as described hereinabove, the resultant West Nile vaccine composition is safened for use in equidae, particularly horses, even for use in pregnant mares, while demonstrating important efficacy as well. Thus, the invention achieves the concomitant goals of effective immunization and safety, especially for pregnant animals. This combination of active immunogen and adjuvant is unheralded in the art.

Pharmacologically acceptable carriers suitable for use in the vaccine composition of the invention may be any conventional liquid carrier suitable for veterinary pharmaceutical compositions, preferably a balanced salt solution or other water-based solution suitable for use in tissue culture media. Other available carriers may also be utilized.

Additional excipients available in the art may also be Included in the vaccine composition according to the various embodiments heretofore described. For example, pH modifiers may be utilized.

The components of the vaccine composition of the invention as heretofore described, including the carrier, may be combined together using available techniques.

In addition to the immunogenically active component of West Nile virus as described hereinabove as active ingredient, it is contemplated that the vaccine composition of the invention may also contain other active components such as an antipathogenic component directed against rabies virus, Eastern equine encephalitis virus, Western equine encephalitis virus, Venezuelan equine encephalitis virus, equine herpes virus such as EHV-1 or EHV-4, *Ehrlichia risticii, Streptococcus equi*, tetanus toxoid, equine influenza virus (EIV), or the like or a combination thereof. The quantities of one or more of these viruses may be determined from efficacy literature in the art, or determined using available techniques.

In one embodiment of the invention the immunogenically active component of the invention may be incorporated into liposomes using known technology such as that described in Nature, 1974, 252, 252-254 or Journal of Immunology, 1978, 120, 1109-13. In another embodiment of the invention, the immunogenically active component of the invention may be conjugated to suitable biological compounds such as polysaccharides, peptides, proteins, or the like, or a combination thereof.

In a preferred embodiment of the invention, the inventive vaccine composition may be formulated in dosage unit form as heretofore described to facilitate administration and ensure uniformity of dosage. Formulation may be effected using available techniques, such as those applicable to preparations of emulsions.

The inventive vaccine composition may be administered parenterally, for example, intramuscularly, subcutaneously, intraperitoneally, intradermally or the like, preferably intramuscularly; or said composition may be administered orally or intranasally.

Accordingly, the present invention also provides a method for the prevention or amelioration of West Nile encephalitis in equidae, preferably horses, which comprises administering to said equidae a safened vaccine composition as described hereinabove.

In actual practice, the vaccine composition of the invention is administered parenterally, subcutaneously, orally, intranasally, or by other available means, preferably parenterally, more preferably intramuscularly, in effective amounts according to a schedule which may be determined by the time of anticipated potential exposure to a carrier of the West Nile virus. In this way, the treated animal may have time to build immunity prior to the natural exposure. By way of non-limiting example, a typical treatment schedule or dosing regimen may include parenteral administration, preferably intramuscular injection of one dosage unit, at least about 2-8 weeks prior to potential exposure. At least two administrations are preferred, for example one dosage unit at about 8 weeks and a second dosage unit at about 3-5 weeks prior to potential exposure of the treated animal. As heretofore set forth, a dosage unit will typically be within the range of about 0.1 to 10 milliliters of vaccine composition containing the previously described amounts of active and percentages of adjuvant and inactive(s) as set forth. A dosage unit within the range of about 0.5 to 5 milliliters is perhaps more preferred, with about 1 to 2 milliliter(s) being particularly preferred.

For a clearer understanding of the invention, the following examples are set forth below. These examples are merely illustrative and are not understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

EXAMPLE 1

Preparation of Vaccine

A/Formulation of SP Oil

| Ingredient Description | Volume |
|---|---|
| Polyoxyethylene-polyoxypropylene block copolymer (Pluronic ® L121, BASF, Mt. Olive, NJ) | 20.0 ml |
| Squalane (Kodak, Rochester, NY) | 40.0 ml |
| Polyoxyethylenesorbitan monooleate (Tween ® 80, Sigma Chemical, St. Louis, MO) | 3.2 ml |
| Buffered salt solution (D-V PBS Solution, Ca, Mg free) | 936.8 ml |

The ingredients are mixed and homogenized until a stable mass or emulsion is formed. Prior to homogenization, the ingredients or mixture may be autoclaved. The emulsion may be further sterilized by filtration. Formalin may be added up to a final concentration of 0.2%. Thimerosal may be added to a final dilution of 1:10,000.

B/Vaccine Preparation

An equine isolate of West Nile virus, obtained from USDA facilities in Ames, Iowa (Lot No. VM-2, Equine Origin, 1999 North American isolate, second passage in VeroM cell culture), was cultivated in multiple cultures of Vero cells in OptiMEM (LTI, Grand Island, N.Y.) tissue culture medium at 37° C. The harvests are titrated and then inactivated by means of addition of a 10% formalin solution to a final concentration of 0.1%. This is allowed to inactivate at 37° C. for a period of no less than 144 hours. Then, another addition of 0.1% formalin is added and incubated at 37° C. for another period of no less than 144 hours.

The vaccines are formulated by suspending the appropriate volume of inactivated virus fluid in 1-20% by volume of SP oil per 1 mL dose.

EXAMPLE 2

Evaluation of Antibody Response to the Intramuscular Injection of Test Vaccine In this evaluation, horses are randomly divided into four groups: one group of twenty horses is administered test vaccine at a dose of $1 \times 10^7$ TCID$_{50}$ (Tissue Culture Infectious Dose); a second group of twenty horses is administered test vaccine at a dose of $5 \times 10^7$ TCID$_{50}$; a third group of five horses is administered test vaccine at a dose of $1 \times 10^8$ TCID$_{50}$; and a fourth group of eight horses are maintained as non-vaccinated environmental controls. Treated horses are given a first dose of vaccine according to the group to which they are assigned. At twenty-one days following administration of the first dose, a second dose of the same vaccine is administered. All horses are bled for serum at the time of administration of the first and second dose and at weekly intervals through 28 days post second dose administration.

Test Vaccine A

| Component | Conc./Dose | Volume/mL |
|---|---|---|
| West Nile virus-Inactivated | $1 \times 10^7$ TCID$_{50}$ | 0.0347 mL |
| MEM[1] | NA | 0.9138 mL |
| SP oil | 5% | 0.0500 mL |
| Polymyxin B[2] | 30.0 mcg/mL | 0.0003 mL |
| Neomycin | 30.0 mcg/mL | 0.0003 mL |
| Thimerosal (5%) | 1:20,000 | 0.0010 mL |

Test Vaccine B

| Component | Conc./Dose | Volume/mL |
|---|---|---|
| West Nile virus-Inactivated | $5 \times 10^7$ TCID$_{50}$ | 0.1734 mL |
| MEM | NA | 0.7752 mL |
| SP oil | 5% | 0.0500 mL |
| Polymyxin B[2] | 30.0 mcg/mL | 0.0002 mL |
| Neomycin[3] | 30.0 mcg/mL | 0.0002 mL |
| Thimerosal[4] (5%) | 1:20,000 | 0.0010 mL |

Test Vaccine C

| Component | Conc./Dose | Volume/mL |
|---|---|---|
| West Nile virus-Inactivated | $1 \times 10^8$ TCID$_{50}$ | 0.3467 mL |
| MEM[1] | NA | 0.6019 mL |
| SP oil | 5% | 0.0500 mL |
| Polymyxin B[2] | 30.0 mcg/mL | 0.0002 mL |
| Neomycin[3] | 30.0 mcg/mL | 0.0002 mL |
| Thimerosal[4] (5%) | 1:20,000 | 0.0010 mL |

[1]LTI, Grand Island, NY
[2]Sigma, St. Louis, MO
[3]Sigma, St. Louis, MO
[4]Sigma, St. Louis, MO The serological data obtained is shown in Table I below, wherein: 0 DPV 1 designates day zero, pre vaccination; and 14 DPV 2 designates day 14, post vaccination. NR designates no results.

As can be seen from the data on Table I, treated horses from all groups showed significant increases in antibodies to West Nile virus while the control horses maintained a non-detectable antibody level. The level of response in the horses that received vaccine was independent of the level of antigen in the vaccine that they received.

TABLE I

| Test Vaccine | Dose (TCID$_{50}$) | Test #1 0DPV1 | Test #1 14DPV2 | Test #2 0DPV1 | Test #2 14DPV2 |
|---|---|---|---|---|---|
| A | $1 \times 10^7$ | <10 | 160 | <10 | 80 |
| A | $1 \times 10^7$ | <10 | 20 | <10 | 10 |
| A | $1 \times 10^7$ | <10 | ≧320 | <10 | 40 |
| A | $1 \times 10^7$ | <10 | 80 | <10 | ≧320 |
| A | $1 \times 10^7$ | <10 | 80 | <10 | 40 |
| A | $1 \times 10^7$ | <10 | 80 | <10 | 160 |
| A | $1 \times 10^7$ | <10 | 40 | <10 | 40 |
| A | $1 \times 10^7$ | <10 | 80 | <10 | 80 |
| A | $1 \times 10^7$ | <10 | 160 | <10 | 80 |
| A | $1 \times 10^7$ | <10 | 40 | <10 | 10 |
| A | $1 \times 10^7$ | <10 | 40 | <10 | 10 |
| A | $1 \times 10^7$ | <10 | 160 | <10 | 40 |
| A | $1 \times 10^7$ | <10 | ≧320 | <10 | NR* |
| A | $1 \times 10^7$ | <10 | ≧320 | <10 | NR |
| A | $1 \times 10^7$ | <10 | ≧320 | <10 | 80 |
| A | $1 \times 10^7$ | <10 | 160 | <10 | 20 |
| A | $1 \times 10^7$ | ≧20 | ≧320 | <10 | 160 |
| A | $1 \times 10^7$ | <10 | 80 | <10 | 80 |
| A | $1 \times 10^7$ | <10 | 80 | <10 | 160 |
| A | $1 \times 10^7$ | <10 | 160 | <10 | 160 |
| B | $5 \times 10^7$ | <10 | 80 | <10 | 40 |
| B | $5 \times 10^7$ | <10 | 20 | <10 | <10 |
| B | $5 \times 10^7$ | <10 | ≧320 | <10 | 160 |
| B | $5 \times 10^7$ | <10 | 80 | <10 | ≧320 |
| B | $5 \times 10^7$ | <10 | ≧320 | <10 | 160 |
| B | $5 \times 10^7$ | <10 | 80 | <10 | 80 |
| B | $5 \times 10^7$ | <10 | 160 | <10 | ≧320 |
| B | $5 \times 10^7$ | <10 | 80 | <10 | 40 |
| B | $5 \times 10^7$ | <10 | 160 | <10 | 40 |
| B | $5 \times 10^7$ | <10 | 40 | <10 | 80 |
| B | $5 \times 10^7$ | <10 | 20 | <10 | 20 |
| B | $5 \times 10^7$ | <10 | ≧320 | <10 | 160 |
| B | $5 \times 10^7$ | <10 | ≧40 | <10 | ≧320 |
| B | $5 \times 10^7$ | <10 | 80 | <10 | 40 |
| B | $5 \times 10^7$ | <10 | 80 | <10 | NR |
| B | $5 \times 10^7$ | <20 | ≧320 | <10 | 80 |
| B | $5 \times 10^7$ | ≧20 | 160 | <10 | 80 |
| B | $5 \times 10^7$ | <10 | ≧320 | <10 | 160 |
| B | $5 \times 10^7$ | <10 | ≧320 | <10 | ≧320 |
| B | $5 \times 10^7$ | <10 | 80 | <10 | 160 |
| C | $1 \times 10^8$ | <10 | ≧320 | <10 | ≧320 |
| C | $1 \times 10^8$ | <10 | ≧320 | <10 | 160 |
| C | $1 \times 10^8$ | <10 | 160 | <10 | 80 |

TABLE I-continued

| Test Vaccine | Dose (TCID$_{50}$) | Test #1 0DPV1 | Test #1 14DPV2 | Test #2 0DPV1 | Test #2 14DPV2 |
|---|---|---|---|---|---|
| C | $1 \times 10^8$ | <10 | ≧320 | <10 | NR |
| C | $1 \times 10^8$ | <10 | 40 | <10 | 40 |
| Control | 0 | <10 | <10 | <10 | <10 |
| Control | 0 | <10 | <10 | <10 | <10 |
| Control | 0 | <10 | <10 | <10 | <10 |
| Control | 0 | <10 | <10 | <10 | NR |
| Control | 0 | <10 | <10 | <10 | <10 |
| Control | 0 | <10 | <10 | <10 | <10 |
| Control | 0 | <10 | <10 | <10 | <10 |
| Control | 0 | <10 | <10 | <10 | <10 |

EXAMPLE 3

Evaluation of Safety of Test Vaccine in Horses Under Field Conditions

In this evaluation, 648 healthy male and female horses, including 32 pregnant mares, are vaccinated with a $6 \times 10^6$ TCID$_{50}$ dose of inactivated test vaccine administered as a 1 mL dose vaccination by intramuscular administration and followed in three to four weeks by a second 1 mL dose vaccination. The treated horses are housed and fed using conventional husbandry practices for farm or stable. All treated horses are observed by a veterinarian for 30 minutes following vaccination for immediate reactions such as salivation, labored or irregular breathing, shaking, or anaphylaxis. For two weeks post-vaccination, the horses are observed daily for any delayed reactions such as lethargy, anorexia or unusual swelling at the injection site. Blood samples of 5 to 10 mL are taken by venipuncture from treated horses on the day of first vaccination (day Zero) and at least once more at two or more weeks post second vaccination (day 36 or greater). Serological assays using PRNT[5] testing are performed.

[5] Chang, G. J.; Hunt, A. R. and Davis B., Journal of Virology, 74 pp 4244-5422 (2000).

| | Test Vaccine | |
|---|---|---|
| Component | Conc./Dose | Volume/mL |
| West Nile virus-Inactivated | $6 \times 10^8$ TCID$_{50}$ | 0.21 mL |
| SP oil | 5% | 0.05 mL |
| MEM | N/A | 0.74 mL |

No vaccine-induced safety problems were found in any of the vaccinates, including the pregnant mares. This evaluation demonstrates that the vaccine of the invention is safe for use in horses under field conditions.

EXAMPLE 4

Evaluation of Efficacy of Test Vaccine (Multivalent and Monovalent Preparations) in Horses Under Experimental Conditions The efficacy of a combination vaccine containing killed West Nile virus (WNV) against experimental WNV challenge was evaluated.

A total of 30 horses were allotted into one vaccinated group (20 horses) and one control group (10 horses). Horses in the vaccinated group received intramuscularly two doses of the test vaccine containing killed West Nile virus ($5 \times 10^7$ TCID$_{50}$ per dose with 5% SP oil), influenza virus, encephalomyelitis virus (Eastern, Western and Venezuelan), rhinopneumonitis virus (serotypes 1 and 4), and tetanus toxoid, three weeks apart. Serum samples were collected periodically for antibody response measured by plaque reduction neutralization test (PRNT). Twenty-four (24) days after the second vaccination, all horses were challenged subcutaneously with WNV. After challenge, horses were monitored for rectal temperature and any clinical signs twice daily for two weeks and once weekly thereafter for detection of viremia. Horses were euthanized and necropsied on 21 and 22 DPC. Cerebrospinal fluid (CSF), spinal cord (cervical, thoracic, and lumbar) and brain (frontal, occipital, medulla oblongata, and brain stem) tissue samples were examined for gross pathology and collected for virus isolation.

Fourteen days after the second vaccination, 75% of vaccinated animals seroconverted (titer≧5) with a geometric mean titer of 10 while control animals remained negative (titer<5). The vaccination conferred a significant protection against viremia (a precursor to development of full-blown West Nile Virus disease). Nine out of 10 (90%) controls developed viremia after challenge, while only eight out of 20 (40%) vaccinates had transient viremia, or viremia lasting only a few days at most. Importantly, no WNV disease clinical signs were observed in any of the challenged vaccinated animals throughout the observation period. (Transient febrile responses were observed in one control and two vaccinated horses. However, there was no evidence to suggest these responses were due to WNV infection.) Petechial hemorrhage in white matter and subdural hemorrhage were found in the brain tissue from one control animal. WNV was isolated from the brain but not from CSF and spinal cord samples collected from this animal. No WNV was isolated from any of the tissue samples collected from other challenged horses.

Results from this study demonstrated a significant protection against both viremia and signs of clinical WNV disease in horses vaccinated with the test combination vaccine.

A second study has conducted with a protocol similar to that above, except that a monovalent WNV vaccine (WNV vaccine alone) was utilized, and all horses were challenged with WNV at 12 months after the second vaccination. Nine out of 11 (81.8%) of the controls developed viremia after challenge, while only one out of 19 (5.3%) of the vaccinates had transient viremia. No WNV associated clinical signs were observed in any of the challenged animals throughout the observation period. No febrile responses were observed in any of the challenged horses. No WNV was isolated from any of the tissue or CSF samples collected from any of the challenged horses. (Prior to challenge at the end of the 12 month period, 17 of the nineteen vaccinated horses had plaque reduction neutralization test (PRNT) titers of 5 or greater, while the control group remained negative (<5).)

Results from this second study demonstrate a significant protection (94% of preventable fraction) against viremia in horses vaccinated with the killed monovalent WNV vaccine. These results also demonstrate a long duration of protective immunity.

EXAMPLE 5

Evaluation of Efficacy of DNA Test Vaccine in Horses Under Experimental Conditions This example demonstrates the efficacy of a West Nile Virus (WNV) DNA vaccine, as part of a further embodiment of the invention. The DNA vaccine contained 100 µg of purified DNA adjuvanted with 5% SP oil per 2 mL dose, and was evaluated against experimental WNV challenge.

For the composition of the WNV DNA vaccine, bacterial cells were harvested from a culture passaged 10 times from a master seed using *E. coli* DH10B obtained from Invitrogen (Carlsbad, Calif.) containing a West Nile plasmid pCBWN obtained from the Centers for Disease Control (Fort Collins, Colo.). The bacterial cells were suspended in glucose-tris-EDTA buffer and lysed with sodium hydroxide and sodium dodecyl sulfate. The lysate was neutralized with a potassium acetate solution. The precipitated complex material containing DNA, RNA, cell debris and proteins was removed by filtration. The filtrate was precipitated with the addition of isopropyl alcohol. The precipitate was collected by centrifugation and resuspended in buffer. This process was repeated using ammonium acetate. The precipitate collected was resuspended in buffer and loaded into a chromatography column packed with Polyflo® resin. The column was then washed and the plasmid DNA was eluted from the column. The eluate was finally diafiltered extensively against phosphate buffer saline. The purified plasmid DNA stocks were then shipped for blending. The test vaccine contained 100 µg of plasmid DNA adjuvanted with 5% SP oil.

The horses used for testing were randomly assigned into two groups: 20 animals received the WNV DNA vaccine, and 10 animals were used as controls. The first group were vaccinated intramuscularly with two 2.0 mL doses of vaccine three weeks apart. The control horses received no vaccinations or placebos. One group of horses (9 vaccinates and 5 controls) were challenged 5 weeks after the second vaccination, whereas a second group of horses (11 vaccinates and 5 controls) were challenged 12 weeks after the second vaccination. Briefly, *Aedes albopictus* mosquitoes which had been infected with WNV 12 days prior to the horse challenge, were allowed to feed on each horse for at least 5 minutes. Following challenge, only those mosquitoes which were found to have engorged with blood meals from each horse were frozen at −20° C., and the virus load was titrated as a pool subsequently. Mosquitoes were then homogenized by vortexing using diluent. The homogenate was centrifuged and the supernatant was removed for titration on Vero cells.

After challenge, rectal temperatures were taken twice daily for at least 9 days and clinical signs were monitored twice a day for at least 21 days. Serum samples were taken twice a day for the first 9 days post challenge (DPC); once daily from 10 to 14 DPC and finally at 21 DPC. Virus isolation was performed on serum samples from 0 DPC to 10 DPC for the first challenge group and from 0 DPC to 11 DPC for the second challenge group. The first group of 14 horses and the second group of 16 horses were euthanized and necropsied 28 to 37 DPC and 29 to 38 DPC, respectively. Cerebrospinal fluid (CSF) and tissue samples from the cerebrum, cerebellum and the brain stem were collected for gross pathology and virus isolation.

At 14 days post second vaccination, 6 of 20 vaccinated had a measurable titer of 2 or greater, and one horse had a titer of 5. Vaccination had conferred protection against experimental West Nile challenge using mosquitoes. Viremia was detected in 5 of 5 control animals and 4 of 9 vaccinates in the first challenge group, whereas 4 of 5 controls and 2 of 11 vaccinates were viremic in the second challenge group of horses. The viremia detected was transient, and occurred only within the first six days after challenge. As a whole, viremia was detected in 9 out of 10 (90%) control horses, while only 6 out of 20 (30%) vaccinates were detected with viremia.

No neurological signs attributable to WNV infection were observed in any of the study horses throughout the challenge observation period. No WNV was isolated from any of the tissue samples collected from any of the study horses. One horse from the first challenge group which was euthanized on 7 DPC showed no gross or microscopic evidence of encephalitis or meningitis.

Results from this study demonstrated a significant protection against viremia in horses vaccinated with the test vaccine.

What is claimed is:

1. A method for the prevention or amelioration of West Nile encephalitis in equidae which comprises administering to said equidae a vaccine composition which comprises an effective immunizing amount of West Nile plasmid DNA, wherein said plasmid DNA is pCBWN; an immunogenically stimulating amount of a metabolizable oil; and a pharmacologically acceptable carrier.

2. The method according to claim 1 having said vaccine composition wherein the metabolizable oil is SP oil.

3. The method according to claim 1 wherein said equidae are horses.

4. The method according to claim 3 wherein said horses are pregnant mares.

5. The method according to claim 1 wherein said vaccine composition is administered parenterally.

6. The method according to claim 1 wherein said vaccine composition is administered intramuscularly.

7. The method according to claim 1 wherein the metabolizable oil is SP oil and is present in an amount of about 5% vol/vol.

8. A method for the prevention or amelioration of West Nile encephalitis in equidae, said method comprising administering to said equidae a vaccine composition comprising West Nile virus plasmid DNA, wherein said plasmid DNA is pCBWN, in an amount of about 50 to 3,000 micrograms per dose and an immunogenically stimulating amount of a metabolizable oil.

9. The method of claim 8, wherein said composition comprises about 100 to 1,000 micrograms of said plasmid DNA per dose.

10. The method of claim 9, wherein said composition comprises about 100 to 250 micrograms of said plasmid DNA per dose.

* * * * *